United States Patent [19]

Saphir

[11] 4,004,877
[45] Jan. 25, 1977

[54] HAIR DYE AND ITS USE

[75] Inventor: Johannes R. Saphir, Hamburg, Germany

[73] Assignee: Carl Brehmer & Sohn, Bremen, Germany

[22] Filed: July 28, 1975

[21] Appl. No.: 599,399

Related U.S. Application Data

[63] Continuation of Ser. No. 355,971, April 30, 1973, abandoned.

[30] Foreign Application Priority Data

May 5, 1972 Germany .......................... 2222001
Feb. 22, 1973 Germany .......................... 2308678

[52] U.S. Cl. .......................................... 8/10; 8/11; 8/32
[51] Int. Cl.$^2$ ...................... D06P 3/00; D06P 5/00
[58] Field of Search ........................... 8/10, 11, 32

[56] References Cited

UNITED STATES PATENTS

| 3,088,878 | 5/1963 | Brunner et al. | 167/88 |
| 3,651,931 | 3/1972 | Hsiung | 8/11 |
| 3,824,075 | 7/1974 | Kalopissis et al. | 8/10 |

FOREIGN PATENTS OR APPLICATIONS

| 64,088 | 3/1914 | Austria |
| 2,222,001 | 9/1974 | Germany |
| 2,120,131 | 11/1971 | Germany |
| 372,640 | 12/1963 | Switzerland |
| 929,053 | 6/1963 | United Kingdom |

OTHER PUBLICATIONS

Venkataraman, "The Chemistry of Synthetic Dyes" vol. V (Academic Press, 1971) pp. 475–534.
Rattee and Breuer, "The Physical Chemistry of Dye Adsorption" (Academic Press, 1974) pp. 295–297.
Diserens, "The Chemical Technology of Dyeing and Printing" vol. II, (Reinhold, 1951) pp. 112–132.
Tucker, J. Soc. Cosmet. Chem., 1971, 22, pp. 379–398.

*Primary Examiner*—Joseph L. Schofer
*Assistant Examiner*—A. L. Clingman
*Attorney, Agent, or Firm*—W. G. Fasse; W. W. Roberts

[57] ABSTRACT

The present hair dye is adapted for dyeing, re-dyeing and also for differently dyeing natural as well as artificial hair without showing a difference in the coloring result, or hue. For this purpose so-called oxidation dyes and soluble catalysts especially metal complex compounds are combined in a solvent wherein the components are at least partially solved to produce a solution and/or mixture wherein the proportion by weight of the catalyst is preferably kept below 1%. The hair dye according to the invention is especially suitable for application out of a spraying device such as an atomizer or an aerosol container whereby the pressure supplying means do not contain any oxygen.

12 Claims, No Drawings

HAIR DYE AND ITS USE

This is a continuation of application Ser. No. 355,971 filed: April 30, 1973 now abandoned.

BACKGROUND OF THE INVENTION

The present invention relates to hair dyeing means which are especially simple in their application or use. Dye means for natural hair are known in many combinations. The known dyeing means are especially unsatisfactory for the purpose of dyeing so-called toupees because these known means can be applied only by skilled personnel and even such personnel must employ and pay strict attention to involved directions of use.

It is known that coloring errors may occur due to an incorrect estimation of the color or hue of hair especially where it is necessary to estimate the color of a glued-in toupee and simultaneously the color of the remaining natural colored hair. Similar errors occur where natural hair and synthetic hair are employed simultaneously for instance in a wig. A toupee which has been dyed with a too dark hue as compared to the hue of the remaining natural hair is useless and must be replaced by a new toupee.

The known so-called genuine hair stylist dyes are not useable for gentlemen toupees nor for ladies' wigs because these dyes must be prepared with oxidation means. The oxidation means comprise hydrogen peroxide and similar oxidation means the use of which makes it practically impossible to avoid an after oxidizing effect of the hair dye so that the dyed or colored hair becomes lighter even more quickly than is the case when such dyes are not used.

The so called textile dyes which as such are very good must be applied to the hair piece by means of boiling. In this manner very good dyeing results have been achieved for many years provided that the hair is being dyed prior to its use in making a hair piece. After the hair has been dyed it is mottled and then tied or knotted into a mounting piece. However, as soon as the hair piece is completed the dyes which require boiling can be employed only with large difficulties. One of these difficulties is seen in that the tying knot loosens up when it is immersed in water which in turn results in a relatively quick loss of the hair out of the hair piece. Another disadvantage is seen in that the dyes even attack the textile of the base piece due to the boiling. Thus, it is possible that the toupee becomes prematurely brittle. A third disadvantage resides in the fact that the owner of a toupee tends to wait too long with the redyeing, presumably due to the bother which is involved with the dyeing. As a result, the hue or color difference between the color of the toupee and the color of the remaining natural hair becomes too large to successfully redye the bleached out hairpiece.

So called hair toning means have also been known heretofore, for example so called coloring rinse lotions or even coloring shampoos. However, these hair toning means have only a temporary effect because they do not stick to the individual hair. Accordingly, these toning means bleach out already after a few days. It is also known to use so called spray colors which cover the hair only on the outside so that a washout for example in the rain cannot be avoided.

It is further known that different shades or hues may be accomplished in connection with natural hair as well as with synthetic hair due to the fact that such hair is exposed to the harmful or noxious components of the air. Such components for example stem from the exhaust gases of internal combustion engines and/or from the harmful exhaust gases of oil furnaces. The influence of direct sunlight may also cause different color hues or shades whereby again different shades may result on synthetic hair as compared to genuine hair.

In any event, natural hair as well as synthetic hair is subject to wear and tear resulting from industrial and automotive exhaust gases as well as from the mechanical strain due to brushing and combing of the hair. As a result, the prior art coloring means are used up and in the synthetic hair additional pores are formed.

The German patent publications DAS 2,028,818 and 2,120,131 disclose the use of metal salt solution in connection with hair dyeing. However, these metal salt solutions are employed in two operational steps whereby the metal salts are first applied to the hair or the hair is immersed in the metal salt solution. In the second working step the hair is bleached in the one instance by means of hydrogen peroxide and in the other instance it is colored by means of a mixture of hydrogen peroxide and so-called oxidation dyes.

OBJECTS OF THE INVENTION

In view of the above it is the aim of the invention to achieve the following objects singly or in combination:

to provide a hair dye which avoids the disadvantages outlined above and which may be used for natural hair as well as for synthetic hair in a simple manner;

to provide a hair dye which may be applied by a person not skilled in the art of hair dyeing whereby the application may be for the purpose of retouching or recoloring regardless whether natural and/or synthetic hair is involved and without any bothersome preparations, in other words the preparation of the hair dye by mixing the components immediately prior to its use is to be avoided and the washing of the hair prior to the application of the dye is also to be avoided;

to avoid a rinsing operation where a certain type of application is involved for example where a very weak dye concentration is employed;

to provide a hair dye which may be used in very precise or fine quantities and which may even be applied by means of a brush or by means of an atomizer or even from an aerosol container whereby in the latter instance the dye is applied to the hair by means of a pressure medium;

to provide a hair dyeing liquid which in the form of a solution and/or a mixture is capable to influence natural hair and/or synthetic hair by providing an intimate bond between the dye and the hair due to the fact that the dye enters into the rough surface of the hair and sticks thereto by causing a swelling of the hair or even by entering into a solution with the surface of the hair so that after the solvent has evaporated an overall and uniform coloring tone or shade is achieved which neutralizes any bleaching;

the present dye shall be equally effective where natural and artificial hair are used simultaneously in a toupee or the like;

to provide a hair dye by means of which it is possible to continuously restore or rather retouch the correct hue for example by a recoloring without the aid of professional help whereby the coloring lost due to the influence of light, air, humidity, as well as cleaning and grooming means is restored and thus bleached out hair pieces can be avoided; and to provide a hair dye which is equally useful for male as well as female hair.

SUMMARY OF THE INVENTION

According to the invention there is provided a hair dye comprising oxidation or oxidizing dyes and soluble catalysts, especially metal complex compounds which become effective as catalysts. The combination of components according to the invention may be considered to be partially a solution and partially a mixture whereby the combination may comprise swelling agents in a homogeneous liquid phase solution. Preferably the catalysts are added in quantities less than 1% by weight of the total combination. It has been found that copper sulphate is especially suitable for the present catalyst purposes.

The hair coloring means according to the invention are especially suitable for application by means of atomizers or other pressure spray containers such as aerosol containers employing a pressure medium without the presence of oxygen. This makes the application of the present hair coloring dyes especially simple.

DESCRIPTION OF EXAMPLE EMBODIMENTS

The hair coloring dyes according to the invention comprise the following components:

a. Dye means of the so called oxidation type such as:

$p$ - phenylenediamine $[C_6H_4(NH_2)_2]$
$p$ - Toluylenediamine $[CH_3C_6H_3(NH_2)_2]$
$p$ - aminodiphenylamine $[C_6H_5C_6H_4NH_2]$
4,4' - diaminodiphenylamine $[HN(C_6H_4NH_2)_2]$ and further oxidation dyes as may be taken from the large number of previous suggestions made in the literature for example German patent publication DAS 1,144,879 which mentions 1-methyl-2,5-diaminobenzenesulphate as well as 1,2,4-diamineanisolsulphate. These compounds are set forth under item 3 in the example in quantities ranging from 0.220 to 0.236 grams. Pairs of oxidation dyes which due to a suitable coupling or compounding capability could be mentioned are the following:

0.28 gram 1,4-diamino-2,5-dioxybenzene
+ 0.22 gram 1,3-dioxybenzene or
0.34 gram 1,4-diamino-2-methoxy-5-methylbenzene
+ 0.28 gram 2,4-diaminoanisol and others.

According to the teaching of German patent publication DAS 1,145,746 it is suggested to finish the dyeing process by means of $H_2O_2$. This is to be avoided according to the teaching of the present invention. The same applies with regard to 2,5-tolualenediamine sulphate and 2,4-diaminoanisolsulphate (2.2 grams/2.36 grams) as set forth in the example of German patent publication DAS 1,147,353. In view of German patents 1,149,496; 1,142,045 and German patent publication 1,492,175 the use of diaminepyridine should also be mentioned as suitable for use as items 3 in example 1 of the present disclosure. At least the diaminepyridine could be used along with other respective oxidizing dyes.

The following substances might also be useful as oxidizing or oxidation dyes in accordance with the present teachings 6,7-dioxyindazol may be used as disclosed in the German patent publication 1,492,166 whereby the dyeing process is finished by the aid of sodium bromate. These fluorine derivatives of the known oxidation dyes as disclosed in German patent publication DAS 1,492,167 may also be employed. This applies as well to nitro-p-phenylenediamine. The latter dye is known to coat hair without the use of $H_2O_2$. However, it has been found that the nitro-p-phenylenediamine as used in accordance with the present teaching, that is, in combination with generally known oxidation dyes and catalysts shows a better genuineness. Further, nitro dyes such as 1-(2'-hydroxyethyl)-amine-2-nitro-4-aminobenzene may also be used in combination with other dyes whereby it has been found that a dark brown referred to as mahogany brown may be achieved. Further, 2-nitro-4-amine-N-methylaniline has been found to result in a chestnut brown coloration if it is used as an additive. The present list is not intended to provide a limitation to the exclusion of other oxidation dyes. To the contrary, other oxidation dyes may be used and reference should be made here for example to the derivatives of pyrazolone which are useable by themselves or in the form of additives to other oxidation dyes and reference is made in this connection to the German patent publication DAS 1,492,072.

b. The catalysts employed according to the invention, for example metal compounds are especially such compounds which produce in combination with the substances mentioned under (a) above dark tones. It is not certain whether these metal compounds act as catalysts in the conventional sense of the word and this is not essential for the effect achieved by the invention. It has been found that copper compounds are especially suitable, however, also compounds of iron, manganese, cobalt, nickel, chromium, titanium, tin, hafnium, zinc, vanadium, and zirconium as well as compounds of molybdenum are suitable for the purposes according to the invention.

c. Solvents for the components mentioned above under (a) and (b) are for example isopropanol and including so called solution facilitating agents as well as swelling agents and suitable complex formation agents which keep the metal compounds in solution. Further, the solvents comprise acids or bases for adjusting a ph-value suitable for the hair. The components under this heading may also include thickening agents.

d. If desired the hair dye according to the invention may be combined with pressure media for dispensing the present hair dye whereby, for example, an atomizer or an aerosol container may be used. The present dye may be removed from a supply container or package without the addition of oxygen, whereby the material may be removed, for example, in the form of a so called foam aerosol.

EXAMPLE 1

The following components are mixed with each other in weight proportions, preferably in the sequence listed to form the desired hair dye solution.

| | | |
|---|---|---|
| 1. | 15.5 | water free of oxygen |
| 2. | 1.0 | monoethanolamine |
| 3. | 12.0 | 5% solution of p-aminodiphenylamine in isopropanol |
| 4. | 17.5 | formamide |
| 5. | 1.7 | copper solution comprising |
| | | 4 parts copper sulphate in crystal form |
| | | 4 parts tartaric acid |

| | | |
|---|---|---|
| | | 4 parts monoethanolamine |
| | | 88 parts water free of oxygen |
| 6. | 14.0 | 4% solution of polyvinylpyrollidone in isopropanol |
| 7. | 38.2 | isopropanol |
| | 100.0 | parts by weight |

The solution according to the above Example 1 or rather its components have been coordinated to each other for the retouching or recoloring of a light brown toupee which has been worn for about 6 weeks. In this connection the combination of Example 1 may be modified for the retouching of a toupee which has been worn only for two weeks by using the components listed under 3 and 5 in quantities corresponding to about one third of the given weight proportion or percentages.

In order to dispense a mixture as set forth in Example 1 about 20 parts by weight of a pressure medium such as diflourodichloromethane are used for each 100 parts of the combination according to Example 1. The hair dye of Example 1 may be sprayed onto the hair or it may be brushed or combed into the hair whereupon the latter is left undisturbed for about twenty minutes. No other steps are required and when the spray has had the desired fine distribution for the intended fine or small shading the toupee is directly ready to wear. Where a thicker spray application or a more pronounced shading is intended that is where the concentration of the effective substances corresponds to such more pronounced shading the hairpiece may be wiped off or dabbed by means of a cotton ball or the like. If desired, the hairpiece may be lightly rinsed in a thin shampoo solution.

In view of the foregoing it will be appreciated that the hair dye according to the invention is characterized by the use of oxydation or oxydizing dyes which as such are known, in combination with catalysts, especially catalitically effective metal complex compounds in a homogeneous, liquid phase, whereby the liquid phase may be included in a pressure package and whereby the pressure medium may be a gas in solution, whereby a premature oxidation of the package content, for example, due to access of the oxygen contained in the air, is prevented.

The solvent isopropanol may be replaced by other low alcohols. Further solvents suitable for use in connection with the teaching according to the invention may comprise low esters, ether, ketones and acidic amides. It will be noted that a member of the latter group has been used in the above Example 1 which includes a formamide serving simultaneously as a swelling agent for the keratin.

Thus, the present invention comprises the combination of components which as such and separately are known which components are partially in solution and partially in a mixture whereby the resulting hair dye may be either liquid or it may possibly also be in a paste form or the dye may be rather viscous. Where the just mentioned combination is dispensed from a pressure container the pressure medium should be free of elemental oxygen. Further, thickening agents may be added which may be natural or of the synthetic type whereby these thickening agents may be of the anionic, the cationic, or of the non-ionic type. Suitably such thickening agents are employed which facilitate the dyeing, for example, those of the cationic type as disclosed in German Patent Publications DAS 1,467,990 and DAS 1,492,021.

Generally it is possible to employ thickening means from a large number of available thickening agents while nevertheless keeping the costs within reasonable limits. For example, polymers or copolymers such as polyvinylpyrollidone and the respective vinyl acetate copolymer may be used. The solvents may be varied as to quantity and type depending on the compounds to be solved. In any event, the combination according to the invention must have a sufficient homogeneity which may be achieved by shaking the components in a common container so that their reaction with each other and with the hair is assured.

EXAMPLE 2

A wig made of synthetic hair having a pink color shading or tone was sprayed with a dye spray according to the invention having the composition shown below. The wig was then combed and after twenty minutes exposure to the dye spray at room temperature, the wig was washed in water and a shampoo solvent. The resulting color was a beautiful grey-rose. The combination of elements was as follows:

| | | |
|---|---|---|
| | 55.25 g | isopropyl alcohol (isopropanol) |
| | 0.86 g | N - phenyl - p - phenylenediamine |
| | 21.00 g | formamide |
| | 21.27 g | water (demineralized, cooked) |
| | 1.32 g | monoethanolamine |
| | 0.10 g | copper sulphate in crystal form with 5 mole of $H_2O$ |
| | 0.10 g | tartaric acid |
| | 0.10 g | sorbitan - mono - oleate derivative of the type TWEEN 20 ATLAS (RTM) |
| 15.00 to | 25.00 g | flourochlorohydrocarbon of the type F12A as an example pressure medium. |

The mixture of Example 2 forms under the pressure of the gas F12A a clear homogeneous liquid.

EXAMPLE 3

A wig of synthetic hair having a redish blonde color shade was sprayed with a spray dye as set forth below and combed for a few minutes. Thereafter the dye was permitted to be effective for about twenty minutes a room temperature, whereupon the wig was rinsed in lukewarm water with shampoo. The resulting color o the synthetic hair was a medium brown. The coloring did not fade in response to light exposure and wa satisfactorily resistant against the influences of the air components such as exhaust gases. The combination of this example comprises the following components in parts by weight:

|  | | |
|---|---|---|
|  | 55.00 g | isopropanol (isopropyl alcohol) |
|  | 1.37 g | N - phenyl - p - phenylenediamine |
|  | 21.00 g | formamide |
|  | 20.93 g | water (demineralized, cooked) |
|  | 1.36 g | monoethanolamine |
|  | 0.12 g | copper sulfate in crystal form with 5 moles of $H_2O$ |
|  | 0.12 g | tartaric acid |
|  | 0.10 g | TWEEN 20 ATLAS (RTM) |
| 15.00 to | 20.00 g | pressure medium F12A as in example 2 |

This mixture also provided a homogeneous phase in a pressure container for example a pressure bottle.

EXAMPLE 4

A wig of synthetic hair having a gold blonde color tone was sprayed with a dye solution as set forth below. The hair was then dryed in the air and combed for a few minutes whereupon the dye was left to be effective for twenty minutes at room temperature. Thereafter the wig was rinsed and shampooed. The result was a permanent dark ashe blonde color shade or tone. The combination was as follows:

|  | | |
|---|---|---|
|  | 55.00 g | isopropanol |
|  | 0.87 g | ortho - phenylenediamine |
|  | 0.52 g | p.p. - diaminediphenylamine sulphate |
|  | 0.35 g | N - phenyl - p - phenylenediamine |
|  | 21.00 g | formamide |
|  | 1.36 g | monoethanolamine |
|  | 20.60 g | water (demineralized, cooked out) |
|  | 0.10 g | copper sulphate (crystals with 5 moles of $H_2O$) |
|  | 0.10 g | tartaric acid |
|  | 0.10 g | TWEEN 20 ATLAS (RTM) |
| 15.00 to | 25.00 g | pressure medium e.g. F12A as in example 2 |

This mixture also formed a homogeneous phase in a pressure container.

The advantages of the invention are seen in that the dye according to the invention may be sprayed onto the hair in a very thin application, whereby a following treatment may not be necessary, for example extensive washing. Another advantage is seen in that the present dye is exceptionally suitable to cover up the boundary between natural hair and a toupee which boundary keeps changing due to the growing of the natural hair, whereby the spraying is exceptionally simple and avoids difficult and time consuming work steps. Even more important, the toupee owner can be certain that the toupee is not recognizable where the boundary between the toupee and the natural hair has been covered by a dye according to the invention. Even female hair which has been used in the making of toupees for men may be dyed in such a manner that the female hair which by nature has a larger proportion of red hues than male hair, will take on the ash or mat hue of male hair. Further, it is possible to retouch or recolor men toupees whereby the problem has been solved residing heretofore in the fact that men toupees have faded much more quickly than ladies wigs because the toupees contact the skin of the head much closer. Even the smallest color deviations may be equalized in a simple manner by employing a atomizer or an aerosol container with a dye according to the invention, whereby a very thin coating of the present dye is sufficient whereby a crass distinction between light and dark is prevented.

In comparison with prior art hair dyes which are known as so called metal hair dyes the invention has also essential advantages which are seen especially in that a preparation and mixing of the hair dye from the individual components immediately prior to its use has been avoided. Further, the known metal hair dyes comprise a metal content which is higher by a power of 10 as compared to the dye according to the invention even if the latter involves its darkest shades. This has the further advantage that according to the invention the unnatural metallic color effects of the known metal dyes have been avoided. Further, the separate storage of the individual components prior to use has also been avoided according to the invention. This in turn avoids the disadvantage that prior art hair metal dyes cannot be stored for any length of time. Even the mixing of dye powders with hot water has been avoided according to the invention.

A further advantage of the invention is seen in that even toupees or wigs in which natural as well as synthetic hair has been intermixed can be treated in a simple manner by a dye as disclosed herein, whereby even after a relatively prolonged wearing time no distinction can be seen in the color hue or shade or in the surface brilliance. It has been found that even body perspiration and cleaning means as well as disinfecting means which do not comprise any harmful, aggressive components do not change the advantageous color effect achieved by a dye as disclosed herein.

Even in connection with artificial or synthetic hair wigs it is merely necessary to somewhat loosen the hairdo, for example, by combing prior to the spraying so that the sprayed dye may penetrate into the hairdo as much as possible, for example, to a depth to which a bleaching may have taken place prior to employing the dyes according to the invention. The present dyes may also be used in a simple manner for redying a wig whereby the spray should penetrate all the way to the bottom or body of the wig.

A further advantage of the invention is seen in that natural as well as synthetic hair may be treated in the same manner with the same results although artificial hair is distinguished from natural hair in its chemical composition and is made up of different base materials. The synthetic hair has microscopically small grooves and pores which in their shape deviate from those of the natural hair, but nevertheless permit a penetration by the liquid hair dye according to the invention in a manner which is comparable to that noted in connection with natural hair.

A further advantage is seen in that the hair dye according to the invention is not only suitable for the restoring of the original color or shade after a bleaching of the natural or synthetic hair, but it may also be used to provide different coloring shades in a satisfactorily permanent manner. This is especially important in connection with wigs which have a color shade substantially deviating from the natural shade in accordance with temporarily prevailing fads. When the fad changes, the wig may easily be redyed in accordance with the present teaching.

The present hair dye may also be dispensed from simple spray bottles having a valve and which may be compressed by hand since these bottles are flexible enough for this purpose. Such bottles with thin flexible walls are well known. As mentioned, where the present dye is dispensed from aerosol containers the pressure medium should preferably not contain any free oxygen. The so called atomizers which employ a pressure ball attachable to the bottle neck together with a spraying device may also be employed for dispensing the present dyes, whereby air is pressed into the container only at the time of removing the dye from the container and the air leaves the container together with the hair dye.

Although the invention has been described with reference to specific example embodiments, it is to be understood, that it is intended to cover all modifications and equivalents within the scope of the appended claims.

What is claimed is:

1. An air oxidation hair dye for reconstituting natural and synthetic hair, comprising the following components in percent by weight:

|  |  |  |
|---|---|---|
|  | 15.5 | water free of oxygen |
|  | 1.0 | monoethanolamine |
| about 4.0 to about | 12.0 | 5% solution of p-aminodiphenylamine in isopropanol |
|  | 17.5 | formamide |
| about 0.56 to about | 1.7 | copper solution comprising 4 parts copper sulphate in crystal form 4 parts tartaric acid 4 parts monoethanolamine 88 parts water free oxygen |
|  | 14.0 | 4% solution of polyvinylpyrollidone in isopropanol and |
|  | 38.3 | isopropyl alcohol. |

2. The air oxidation hair dye of claim 1, comprised in a container and including 15 to 20 grams of a pressure medium.

3. An air oxidation hair dye for reconstituting natural and synthetic hair, comprising the following components in percent by weight:

| | |
|---|---|
| 55.25 | isopropyl alcohol |
| 0.86 | N-phenyl-p-phenylenediamine |
| 21.00 | formamide |
| 21.27 | distilled water |
| 1.32 | monoethanolamine |
| 0.10 | copper sulphate in crystal form with 5 mole of $H_2O$ |
| 0.10 | tartaric acid as said complex forming agent and |
| 0.10 | sorbitan-mono-oleate derivative. |

4. The air oxidation hair dye of claim 3, comprised in a container and including 15 to 25 grams of a pressure medium.

5. An air oxidation hair dye for reconstituting natural and synthetic hair, comprising the following components in percent by weight:

| | |
|---|---|
| 55.00 | isopropyl alcohol |
| 1.37 | N-phenyl-p-phenylenediamine |
| 21.00 | formamide |
| 20.93 | distilled water |
| 1.36 | monoethanolamine |
| 0.12 | copper sulphate in crystal form with 5 moles of $H_2O$ |
| 0.12 | tartaric acid and |
| 0.10 | sorbitan-mono-oleate derivative. |

6. The air oxidation hair dye of claim 5, comprised in a container and including 15 to 20 grams of a pressure medium.

7. An air oxidation hair dye for reconstituting natural and synthetic hair, comprising the following components in percent by weight:

| | |
|---|---|
| 55.00 | isopropyl alcohol |
| 0.87 | ortho-phenylenediamine |
| 0.52 | p.p.-diaminediphenylamine sulphate |
| 0.35 | N-phenyl-p-phenylenediamine |
| 21.00 | formamide |
| 1.36 | monoethanolamine |
| 20.60 | distilled water |
| 0.10 | copper sulphate (crystals with 5 moles of $H_2O$) |
| 0.10 | tartaric acid and |
| 0.10 | sorbitan-mono-oleate derivative. |

8. The air oxidation hair dye of claim 7, comprised in a container and including 15 to 20 grams of pressure medium.

9. A hair dye for reconstituting natural and synthetic hair, consisting of an air oxidation hair dye, a metal complex compound and a solvent which keeps the air oxidation hair dye and the metal complex compound in solution, said metal complex compound consisting of a metal present in a quantity ranging from 0.1% to less than 1% by weight and selected from the group consisting of copper, iron, manganese, cobalt, nickel, chromium, titanium, tin, hafnium, zinc, vanadium, zirconium and molybdenum; a complex forming agent present in the weight percent range corresponding to that of said metal quantity given above, and monoethanolamine ranging from 1.0% to 1.36% by weight, said solvent ranging from 38.3% to 55.25% by weight, said solvent comprising formamide said percent by weight referring to the weight of the total composition.

10. The air oxidation hair dye of claim 9, wherein said copper metal is present in the form of copper sulphate, said complex forming agent is tartaric acid, and wherein said solvent includes isopropyl alcohol and said formamide.

11. The air oxidation hair dye of claim 9, wherein said formamide constitutes about 17.5% by weight to about 21.0% by weight of the total composition.

12. A method of air oxidation dyeing natural and synthetic hair comprising applying to said hair a dye consisting of an air oxidation dye, a metal complex compound and a solvent which keeps the air oxidation hair dye and the metal complex compound in solution, said metal complex compound consisting of a metal present in the quantity ranging from 0.1% to less than 1% by weight and selected from the group consisting of copper, iron, manganese, cobalt, nickel, chromium, titanium, tin, hafnium, zinc, vanadium, zirconium and molybdenum; a complex forming agent present in the weight percent range corresponding to that of said metal quantity given above, and monoethanolamine ranging from 1.0% to 1.36% by weight, said solvent ranging from 38.3% to 55.25% by weight, said solvent comprising formamide said percent by weight referring to the weight of the total composition, and leaving the hair with said dye applied thereto undisturbed for a length of time up to about 20 minutes.

* * * * *